United States Patent [19]

Exton

[11] 3,931,462

[45] Jan. 6, 1976

[54] STACK PLUME VISUALIZATION SYSTEM

[75] Inventor: Reginald J. Exton, Williamsburg, Va.

[73] Assignee: The United States of America as represented by the United States National Aeronautics and Space Administration Office of General Counsel-Code GP, Washington, D.C.

[22] Filed: Mar. 11, 1975

[21] Appl. No.: 557,448

[52] U.S. Cl. ........ 178/6.8; 178/DIG. 1; 178/DIG. 8; 250/373; 340/237 S; 356/207
[51] Int. Cl.² .......................................... H04N 7/18
[58] Field of Search............ 178/6.8, DIG. 1, DIG. 8; 340/237 S; 250/373; 356/207

[56] References Cited
UNITED STATES PATENTS 3,795,812  3/1974  Okabe................................. 250/373
3,841,763  10/1974  Lewis................................. 356/207

Primary Examiner—Robert L. Griffin
Assistant Examiner—Edward L. Coles
Attorney, Agent, or Firm—William H. King; Howard J. Osborn; John R. Manning

[57] ABSTRACT

This invention is method and apparatus for measuring, at a remote location, the concentration and velocity of $SO_2$ in plume from a smokestack. An ultraviolet video system views the plume against the background sky at wavelengths where $SO_2$ molecules absorb light. The result is a real time display of the plume coupled with means for measuring the $SO_2$ concentration at any point in the plume and at any time desired. In addition, means are provided in combination with the ultraviolet video system for measuring the velocity of the $SO_2$ in the plume.

13 Claims, 3 Drawing Figures

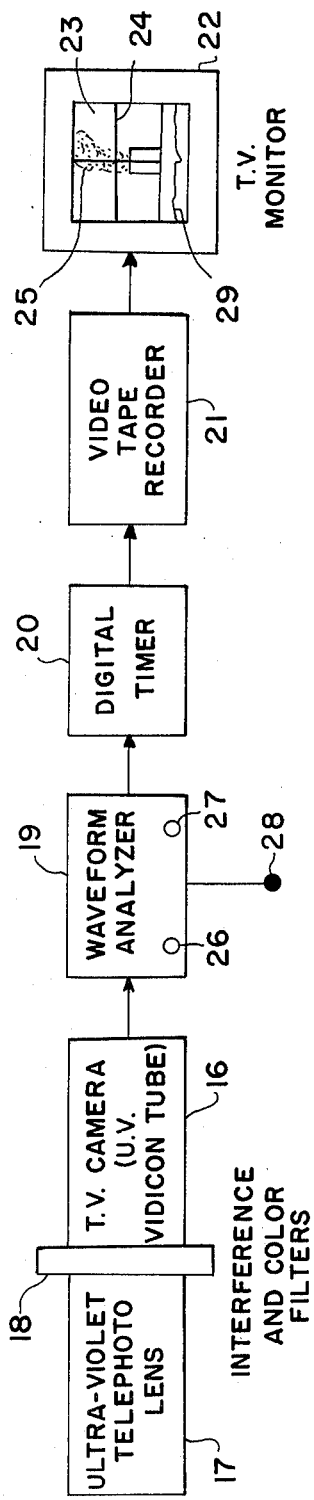
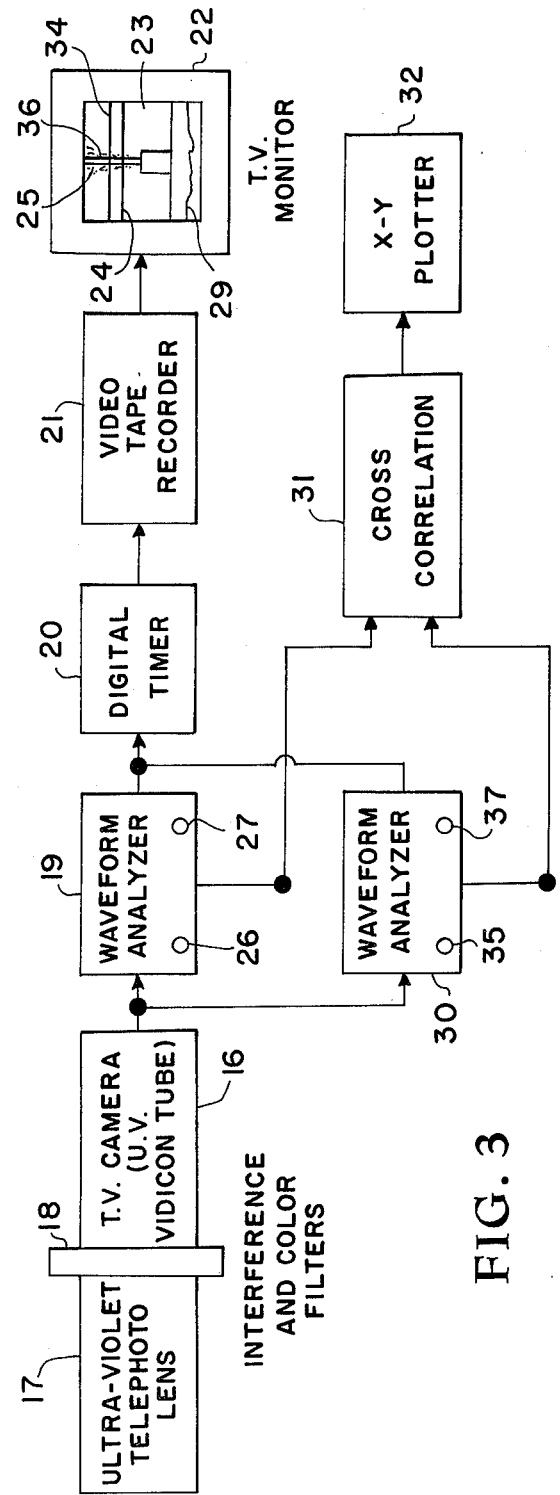

STACK PLUME VISUALIZATION SYSTEM

ORIGIN OF THE INVENTION

The invention described herein was made by an employee of the National Aeronautics and Space Administration and may be manufactured and used by or for the Government for governmental purposes without the payment of any royalties thereon or therefor.

BACKGROUND OF THE INVENTION

In the future, it is likely that pollution monitoring agencies will require remote measuring techniques for many pollutants in order to properly monitor and control the environment. In the area of power plant smokestack effluents, the three major concerns are the particulates (fly ash), the NO and the $SO_2$ emissions. Many techniques are presently being developed to remotely measure these effluents, such as laser radars, I. R. systems and correlation spectrometers. These devices are in various states of development; all are very expensive and difficult to operate and practically all suffer from a commmon problem, plume instability. This refers to the dynamic character of the plume which is a function of the exit velocity, ambient wind conditions and uniformity of the stack flow. An extreme case of these conditions is represented by the downwash situation which can cause serious deviations in the plume dimensions and hence in any effluent monitor's output signal. Of course, the change in signal cannot normally be attributed to the changes in plume geometry, but would more than likely be attributed to variations in the particular effluent's concentration.

It is therefore a primary object of this invention to provide a method and apparatus for measuring, at a remote location, smokestack effluents.

Another object of this invention is to provide a method and apparatus for measuring, at a remote location, the $SO_2$ concentration at any selected point in the plume of a smokestack.

A further object of this invention is to provide a method and apparatus for measuring, at a remote location, the velocity of the emission of $SO_2$ from a smokestack.

Other objects and advantages of this invention will further become apparent hereinafter and in the drawings.

SUMMARY OF THE INVENTION

This invention is a method and apparatus for measuring at a remote location the concentration and velocity of the $SO_2$ in plume from a smokestack. An ultraviolet video system views the plume against the background sky at wavelengths where $SO_2$ molecules absorb light. The resulting signals are applied to a waveform analyzer which is used to measure the $SO_2$ concentration at any selected point in the plume. The video signals are also applied to a video tape recorder and TV monitor and the scene on the monitor is recorded. By employing slow-motion video playback techniques the resulting recordings are used to measure the velocity of $SO_2$ by determining the velocity of the fluctuations (relatively heavier concentrations) of the $SO_2$ through the plume. In an alternate embodiment of the invention the velocity of the $SO_2$ is determined by using two waveform analyzers to produce two signals representing the concentration of $SO_2$ at two selected points in the direction of flow of the plume and cross-correlating the two signals. This cross-correlation gives the average time that it takes fluctuations to move between the two selected points.

BRIEF DESCRIPTION OF THE DRAWINGS

FIG. 2 is a block diagram of an embodiment of the invention; and

FIG. 3 is a block diagram of another embodiment of the invention.

DETAILED DESCRIPTION OF THE INVENTION

Figure 1:
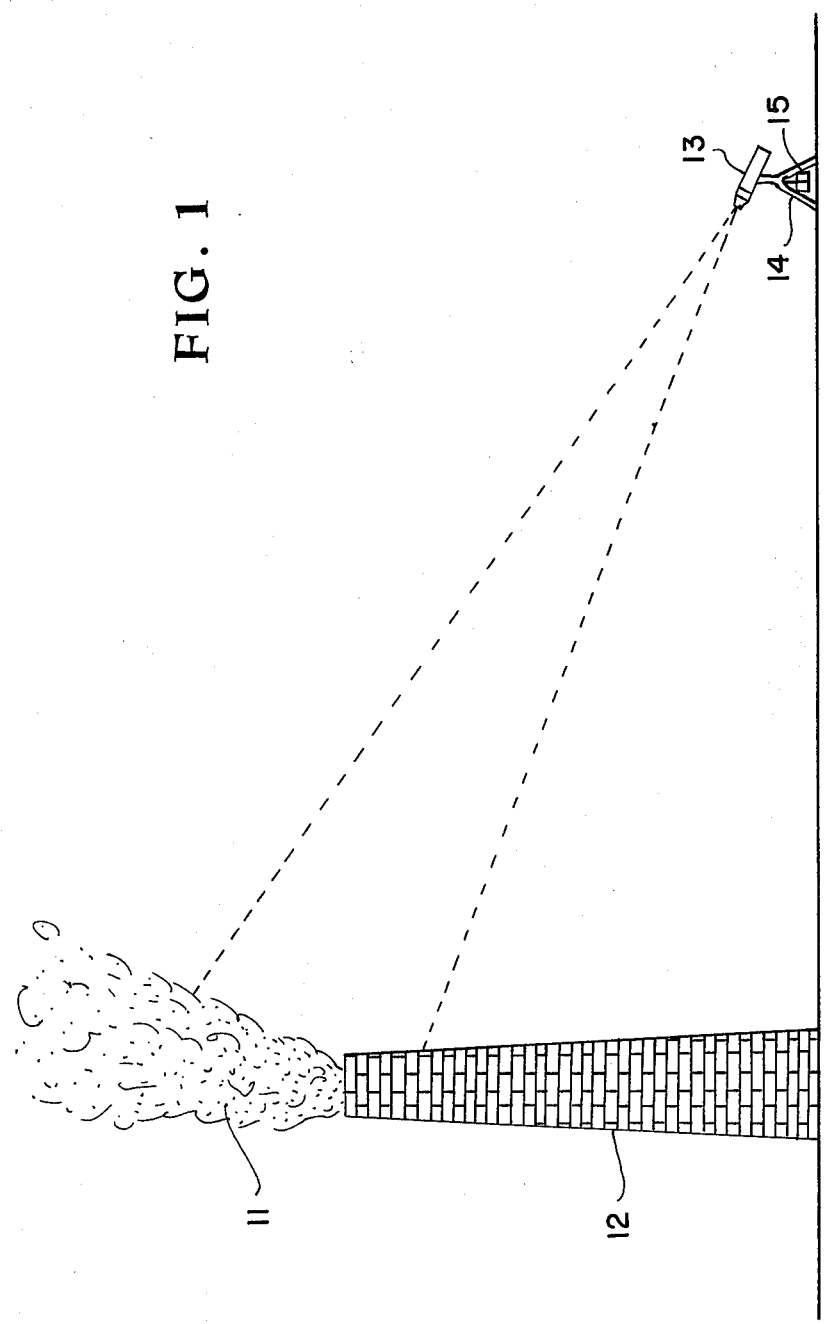
FIG. 1 is a schematic drawing for the purpose of showing how the invention operates.

The purpose of the invention is to measure from a remote location the $SO_2$ emission in the plume 11 of a smokestack 12. The invention can also be used to measure fly ash and $NO_2$ emissions; however, since $SO_2$ is of greater concern the invention will be described as making measurements of $SO_2$. A TV system 13 including an untraviolet vidicon tube, an ultraviolet telephoto lens, and interference and color filters is located at the remote location and is supported by a suitable means such as a tripod 14. The output of the TV camera system 13 is fed into an electronic package 15 where it is processed. The camera system 13 is adjusted so that its field-of-view includes the uppermost part of stack 12 and part of the plume.

The operation of the invention depends on the amount of untraviolet light from the background sky that is absorbed by plume 11 and therefore does not reach the camera system 13. The plume absorbs ultraviolet light because of fly ash, $NO_2$ and $SO_2$ contained therein. However, at wavelengths of approximately 3,150 angstroms there is substantial absorption by $SO_2$, negligible absorption by $NO_2$ and a small mount of absorption by fly ash. Hence, this invention is operable in the 3,150 angstroms region to measure $SO_2$. The error in the measurements due to fly ash can be corrected by determining at other wavelengths the effect of fly ash on an absorption measurement.

Turning now to the embodiments of the invention selected for illustration in the drawings the number 16 in FIG. 2 designates a TV camera including an ultraviolet vidicon tube. The camera is equipped with an ultraviolet telephoto lens 17, and interference and color filters 18. The output of camera 16 is applied through a waveform analyzer 19, a digital timer 20, and a video tape recorder 21 to a TV monitor 22. The field-of-view of camera 16 is displayed as picture 23 on TV monitor 22. The waveform analyzer 19 superimposes a horizontal cursor 24 and a vertical cursor 25 on picture 23. The positions of cursors 24 and 25 are controlled by knobs 26 and 27, respectively. The amount of the background skylight that reaches camera 16 at the point of intersection of cursors 24 and 25 is represented by an electrical signal at output terminal 28. The amount of the background skylight that reaches the camera along cursor 24 is represented by the curve 29 on the face of the TV monitor. The digital timer 20 supplies timing information that is also superimposed on picture 23. The information displayed on TV monitor 22 is recorded by video tape recorder 21. Analyzers suitable for use as waveform analyzer 19 are commercially available. For example, model CVI-302, Colorado Video Incorporated, is suitable for use as waveform analyzer 19.

The apparatus in FIG. 2 provides a real time display of the plume coupled with the means for measuring the $SO_2$ concentration at any time desired. In this way, the plume stability problem can be easily studied and measurements can be made at selected times when optimum conditions exist (i.e., no downwash and relatively uniform flow). In essence, the system senses the flow pattern and delineates its limitations on the measurement. The recordings made by video tape recorder 21 can be used to measure the $SO_2$ velocity in the plume. The recordings contain fluctuations in the concentration of $SO_2$. That is, the recordings contain dark spots which represent larger concentrations of $SO_2$. These dark spots or fluctuations move at the same velocity as the $SO_2$. Hence, by measuring the velocity of these fluctuations a measure of the velocity of the $SO_2$ is obtained. This can be done by employing slow-motion video playback of the recordings made by recorder 21. In this mode a fluctuation in the $SO_2$ concentration can be tracked through the field-of-view of camera 16 and the velocity of the fluctuation can be measured.

The embodiment of the invention shown in FIG. 3 provides means for obtaining the $SO_2$ velocity directly. This embodiment differs from the embodiment in FIG. 2 only in the use of an additional waveform analyzer 30, a cross correlator 31 and an X-Y plotter 32. The output of camera 16 in addition to being applied through waveform analyzer 19 to TV monitor 22 is applied through waveform analyzer 30 to TV monitor 22 to superimpose a horizontal cursor 34 and a vertical cursor 36 on picture 23. The positions of cursors 34 and 36 are controlled by knobs 35 and 37, respectively. The output of analyzer 19 which represents the concentration of the $SO_2$ at the point of intersection of cursors 24 and 25 and the output of analyzer 30 which represents the concentration of the $SO_2$ at the point of intersection of cursors 34 and 36 are applied to cross correlator 31. The output of cross correlator 31 is applied to an X-Y plotter 32. Plotter 32 provides a graph that indicates the average time that it takes fluctuations in $SO_2$ concentration to travel between the points in the plume defined by the intersection of cursors 24 and 25 and the intersection of cursors 34 and 36. Correlators suitable for use as cross correlator 31 are commercially available. For example, Model SA1-43A Saicor/-Honeywell is suitable for use as cross correlator 31.

In the operation of the embodiment of the invention in FIG. 3, the intersection of cursors 34 and 36 is adjusted such that it is in the direction of flow of the plume from the intersection of cursors 24 and 25. The cross correlator 31 and X-Y plotter 32 will then indicate the average time that it takes fluctuations to travel between the two points. This average time in combination with the distance between the two points is indicative of the velocity of the $SO_2$.

The primary advantage of the invention is its ability to "see" the plume in its entirety and to properly assess plume instabilities, and its ability to measure the effluent concentration and velocity at a remote location.

What is claimed is:

1. Apparatus for measuring at a remote location the $SO_2$ concentration in plume from a smokestack comprising:

an ultraviolet video system means for viewing said plume from a remote location against the background sky at wavelengths where $SO_2$ molecules absorb a substantial amount of light and for producing electrical signals representative of the scene viewed, and TV monitor meeans for receiving the output of said video system and for producing a picture of the $SO_2$ concentration in said plume.

2. Apparatus according to claim 1 including waveform analyzer means for superimposing a horizontal cursor and a vertical cursor on said picture.

3. Apparatus according to claim 2 wherein said waveform analyzer means includes means for producing an electrical signal representating the $SO_2$ concentration at the point in said plume represented by the intersection of said horizontal cursor and said vertical cursor.

4. Apparatus according to claim 2 wherein said waveform analyzer means includes means for displaying on said TV monitor a graph of the $SO_2$ concentration along a line in the plume defined by said horizontal cursor.

5. Apparatus according to claim 2 including a digital timer for supplying a timing signal to said TV monitor to provide timing information on said picture.

6. Apparatus according to claim 5 including a video tape recorder for recording the picture displayed on said TV monitor.

7. Apparatus for measuring at a remote location the $SO_2$ velocity in plume from a smokestack comprising:

an ultraviolet video system means for viewing said plume from a remote location against the background sky at wavelengths where $SO_2$ molecules absorb light and for producing electrical signals representative of the scene viewed; and means receiving said electrical signals for measuring the velocity of the fluctuations of $SO_2$ occurring in said plume whereby the velocity of the fluctuations is a measure of the velocity of the $SO_2$ emitted from the smokestack.

8. Apparatus according to claim 7 wherein said means for measuring the velocity of the fluctuations of $SO_2$ occurring in said plume includes a TV monitor and a video tape recorder.

9. Apparatus according to claim 7 wherein said means for measuring the velocity of the fluctuations of $SO_2$ occurring in said plume includes means for producing a first analog signal representing the $SO_2$ concentration passing a first point in said plume, means for producing a second analog signal representing the $SO_2$ concentration passing a second point in said plume said second point being in the line of flow of said plume from said first point, and means receiving said first and second analog signals for determining the time it takes a fluctuation in the $SO_2$ concentration to travel from said first point to said second point.

10. Apparatus according to claim 9 wherein said means for determining time is a cross-correlator receiving said first and second analog signals and an X-Y plotter for plotting the output of said cross-correlator.

11. A method for measuring at a remote location the $SO_2$ concentration in plume from a smokestack comprising the steps of:

taking an ultraviolet video picture, from said remote location, of said plume using skylight as the background at a wavelength of approximately 3,150 angstroms where there is substantial absorption of ultraviolet light by $SO_2$; and measuring at selected points in said picture and at selected times the amount of ultraviolet light in the background skylight absorbed by the plume.

12. A method for measuring at a remote location the velocity of $SO_2$ in plume from a smokestack comprising the steps of:

taking an ultraviolet video picture, from said remote location, of said plume using skylight as the background at a wavelength of approximately 3,150 angstroms where there is substantial absorption of ultraviolet light by $SO_2$; and measuring the velocity of fluctuations in the concentration of $SO_2$ in the video picture whereby the velocity of the fluctuations is the velocity of the $SO_2$.

13. A method according to claim 12 wherein the step of measuring the velocity of fluctuations in the concentration of $SO_2$ includes the steps of measuring at two separate points in the path of the flow of the plume the amount of ultraviolet light in the background skylight absorbed by the plume and cross-correlating the two measurements to obtain the average time that it takes for fluctuations to travel between the two points.

* * * * *